US007163549B2

(12) United States Patent
Crank et al.

(10) Patent No.: US 7,163,549 B2
(45) Date of Patent: Jan. 16, 2007

(54) FILTER MEMBRANE MANUFACTURING METHOD

(75) Inventors: Justin Crank, St. Louis Park, MN (US); Narin Anderson, Savage, MN (US); James G. Hansen, Coon Rapids, MN (US); Horng-Ban Lin, Maple Grove, MN (US); Mark Smith, Coon Rapids, MN (US); The Thomas Trinh Tran, Coon Rapids, MN (US); Kinh-Luan D. Dao, Randolph, MA (US); Yem Chin, Burlington, MA (US); Sheng-Ping Zhong, Northborough, MA (US); James M. Anderson, Monticello, MN (US); Jeffrey H. Vogel, Brooklyn Park, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 529 days.

(21) Appl. No.: 10/364,597

(22) Filed: Feb. 11, 2003

(65) Prior Publication Data

US 2004/0158275 A1 Aug. 12, 2004

(51) Int. Cl.
*A61M 29/00* (2006.01)
(52) U.S. Cl. ...................................... 606/200
(58) Field of Classification Search ................ 606/200; 264/299
See application file for complete search history.

(56) References Cited

U.S. PATENT DOCUMENTS

| 3,472,230 | A | 10/1969 | Fogarty |
|---|---|---|---|
| 3,952,747 | A | 4/1976 | Kimmell, Jr. |
| 3,996,938 | A | 12/1976 | Clark, III |
| 4,046,150 | A | 9/1977 | Schwartz et al. |
| 4,425,908 | A | 1/1984 | Simon |
| 4,590,938 | A | 5/1986 | Segura et al. |
| 4,619,246 | A | 10/1986 | Molgaard-Nielsen et al. |
| 4,650,466 | A | 3/1987 | Luther |
| 4,688,553 | A | 8/1987 | Metals |
| 4,706,671 | A | 11/1987 | Weinrib |
| 4,723,549 | A | 2/1988 | Wholey et al. |
| 4,790,812 | A | 12/1988 | Hawkins, Jr. et al. |
| 4,790,813 | A | 12/1988 | Kensey |
| 4,794,928 | A | 1/1989 | Kletschka |
| 4,807,626 | A | 2/1989 | McGirr |
| 4,848,673 | A | 7/1989 | Masuda et al. |
| 4,873,978 | A | 10/1989 | Ginsburg |
| 4,921,478 | A | 5/1990 | Solano et al. |
| 4,921,484 | A | 5/1990 | Hillstead |

(Continued)

FOREIGN PATENT DOCUMENTS

DE 28 21 048 7/1980

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner*—Anhtuan T. Nguyen
*Assistant Examiner*—Elizabeth Houston
(74) *Attorney, Agent, or Firm*—Crompton, Seager & Tufte LLC (57) ABSTRACT

An embolic protection filter and method of making the same. An embolic protection filter may include a filter membrane or material having a plurality of holes. In some embodiments, the filter membrane may be manufactured by spray coating a filter material onto a forming member or spray mold.

21 Claims, 10 Drawing Sheets

U.S. PATENT DOCUMENTS

| | | | |
|---|---|---|---|
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,064,428 A | 11/1991 | Cope et al. |
| 5,071,337 A | 12/1991 | Heller et al. |
| 5,071,407 A | 12/1991 | Termin et al. |
| 5,100,423 A | 3/1992 | Fearnot |
| 5,102,415 A | 4/1992 | Guenther et al. |
| 5,108,419 A | 4/1992 | Reger et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,350,398 A | 9/1994 | Pavenik et al. |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,518 A | 12/1997 | Laerum |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,779,732 A | 7/1998 | Amundson |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,824,374 A | 10/1998 | Bradley, Jr. et al. |
| 5,827,324 A | 10/1998 | Cassell et al. |
| 5,833,644 A | 11/1998 | Zadno-Azizi et al. |
| 5,833,650 A | 11/1998 | Imran |
| 5,836,969 A | 11/1998 | Kim et al. |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,928,726 A | 7/1999 | Butler et al. |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,968,071 A | 10/1999 | Chevillon et al. |
| 5,980,555 A | 11/1999 | Barbut et al. |
| 5,984,947 A | 11/1999 | Smith |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscroft et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,096,053 A | 8/2000 | Bates |
| 6,117,154 A | 9/2000 | Barbut et al. |
| 6,120,847 A | 9/2000 | Yang et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,153,252 A | 11/2000 | Hossainy et al. |
| 6,156,373 A | 12/2000 | Zhong et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,203,732 B1 | 3/2001 | Clubb et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,261,320 B1* | 7/2001 | Tam et al. ............... 623/1.15 |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,322,847 B1 | 11/2001 | Zhong et al. |
| 6,344,049 B1 | 2/2002 | Levinson et al. |
| 6,361,545 B1 | 3/2002 | Macoviak et al. |
| 6,364,895 B1 | 4/2002 | Greenhalgh |
| 6,375,670 B1 | 4/2002 | Greenhalgh |
| 6,406,471 B1 | 6/2002 | Jang et al. |
| 6,461,370 B1* | 10/2002 | Gray et al. ............... 606/200 |
| 6,468,291 B1 | 10/2002 | Bates et al. |
| 6,485,502 B1 | 11/2002 | Don Michael et al. |
| 6,497,916 B1 | 12/2002 | Taylor et al. |
| 6,616,680 B1* | 9/2003 | Thielen ............... 606/200 |
| 6,702,834 B1* | 3/2004 | Boylan et al. ............... 606/200 |
| 7,029,440 B1* | 4/2006 | Broome et al. ............... 600/200 |

| | | |
|---|---|---|
| 2004/0193208 A1 * | 9/2004 | Talpade et al. ............. 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 914 918 A2 | 5/1999 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |
| WO | WO 02/43595 A2 | 6/2002 |

OTHER PUBLICATIONS

"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).
Cragg, Andrew et al., "Nonsurgical Placement of Arterial Endoprosthesis: A New Technique Using Nitinol Wire," AJR, pp. 261-263 (Apr. 1983).
Diethrich et al., "Percutaneous Techniques for Endoluminal Carotid Interventions," *J. Endovasc. Surg.*, 3:182-202 (1996).
Fadali, A. Moneim, "A filtering device for the prevention of particulate embolization during the course of cardiac surgery," *Surgery*, 64(3):634-639 (Sep. 1968).
Haissaguerre et al., "Spontaneous Initiation of Atrial Fibrillation by Ectopic Beats Originating in the Pulmonary Veins," *The New England Journal of Medicine*, 339(10):659-666 (Sep. 1988).
Jordan, Jr. et al., "Microemboli Detected by Transcranial Doppler Monitoring . . . ," Cardiovascular Surgery, 7(1)33-38 (Jan. 1999).
Lesh, "Can Catheter Ablation Cure Atrial Fibrillation?" *ACC Current Journal Review*, pp. 38-40 (Sep./Oct. 1997).
Lund et al., "Long-Term Patentcy of Ductus Arteriosus After Balloon Dilation: an Experimental Study," Laboratory Investigation, 69(4):772-774 (Apr. 1984).
Marache et al., "Percutaneous Transluminal Venous Angioplasty . . . ," *American Heart Journal*, 125(2 Pt 1):362-366 (Feb. 1993).

Mazur et al., "Directional Atherectomy with the Omnicath™ : A Unique New Catheter System," Catheterization and Cardiovascular Diagnosis, 31:17-84 (1994).

Moussa, MD, Issaam "Stents Don't Require Systemic Anticoagulation . . . But the Technique (and Results) Must be Optimal," Journal of Invasive Cardiol., 8(E):3E-7E, (1996).

Nakanishi et al., "Catheter Intervention to Venous System Using Expandable Metallic Stents," Rinsho Kyobu Geka, 14(2):English Abstracts Only (Apr. 1994).

Onal et al., "Primary Stenting for Complex Atherosclerotic Plaques in Aortic and Iliac Stenoses," Cardiovascular & Interventional Radiology, 21(5):386-392 (1998).

Theron et al., "New Triple Coaxial Catheter System for Carotid Angioplasty with Cerebral Protection," American Journal of Neuroradiology, 11:869-874 (1990).

Tunick et al., "Protruding atherosclerotic plaque in the aortic archo f patients with systemic embolization: A new finding seen by transesophageal echocardiography," *American Heart Journal* 120(3):658-660 (Sep. 1990).

Waksman et al., "Distal Embolization is Common After Directional Atherectomy . . . ," American Heart Journal, 129(3):430-435 (1995).

Wholey, Mark H. et al., PTA and Stents in the Treatment of Extracranial Circulation, *The Journal of Invasive Cardiology*, 8(E):25E-30E (1996).

* cited by examiner

FILTER MEMBRANE MANUFACTURING METHOD

FIELD OF THE INVENTION

The present invention pertains to embolic protection filter assemblies. More particularly, the present invention pertains to improved embolic protection filters and improved methods of manufacturing embolic protection filters.

BACKGROUND

Heart and vascular disease are majors problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

BRIEF SUMMARY

The present invention pertains to embolic protection filter devices and methods of making the same. In some embodiments, an embolic protection filter assembly includes an elongate shaft having an embolic protection filter coupled thereto. The filter may include a filter frame, a filter material, and one or more struts.

A number of methods of manufacturing the filter are also disclosed. One method, for example, includes spray or powder coating a filter material onto a forming member or spray mold. This method may also include spraying multiple layers of filter material and/or incorporating the filter frame or other suitable support structures. Other methods include using a spray mold that includes one or more grooves. A support structure may be disposed in the grooves or the filter material may be spray coated adjacent the grooves. These and other embodiments of filter assembly and manufacturing methods are described in more detail below.

DETAILED DESCRIPTION

The following description should be read with reference to the drawings wherein like reference numerals indicate like elements throughout the several views. The detailed description and drawings illustrate example embodiments of the claimed invention.

When a clinician performs an intravascular intervention such as angioplasty, atherectomy, and the like, embolic debris may dislodge from the blood vessel that can travel in the bloodstream and impair blood flow, possibly leading to tissue damage. A number of intravascular filtering devices have been developed that can be disposed in the blood vessel downstream of the treatment site and expanded to capture debris. Moreover, a number of manufacturing methods have been developed for producing these devices. In at least some embodiments, the present invention pertains to refinements of both embolic protection filters and methods of making them.

Figure 1:
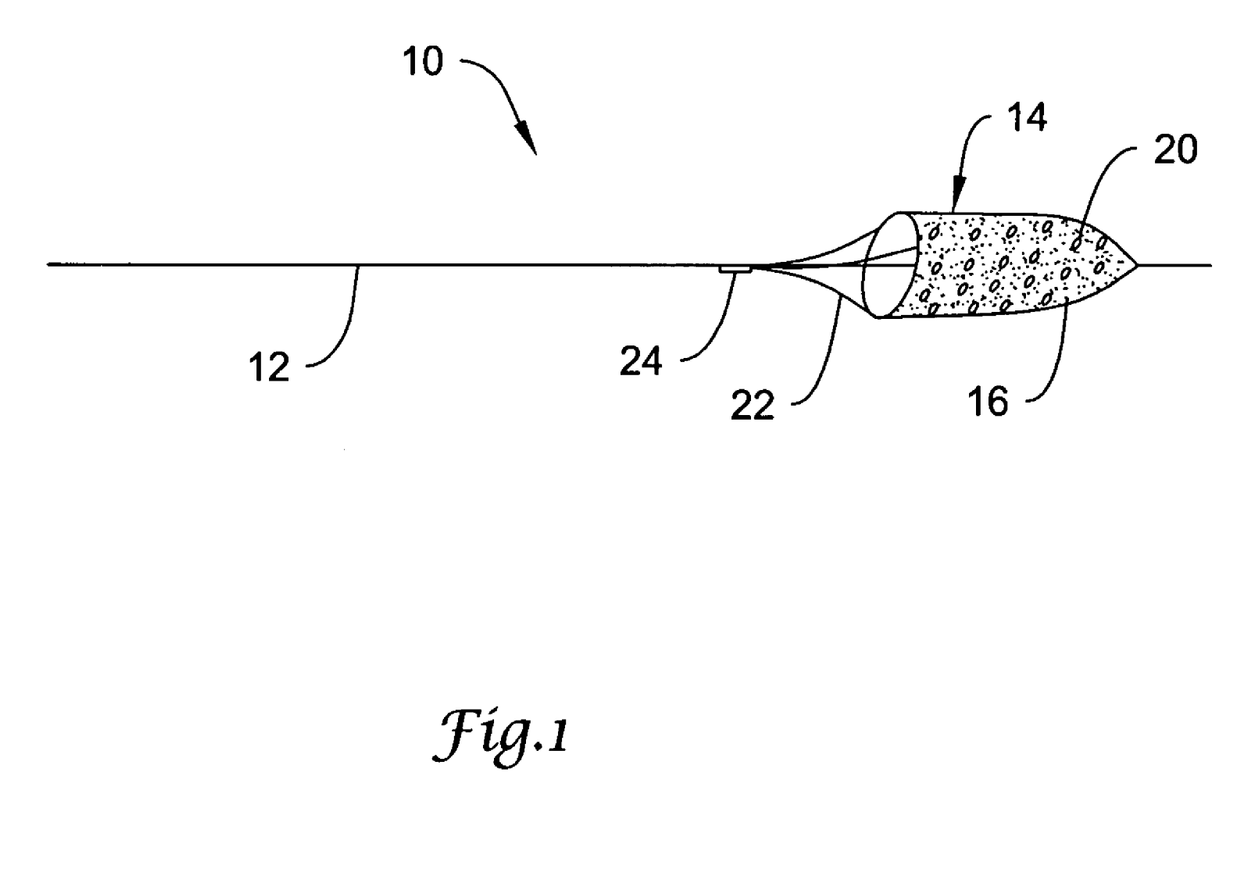
FIG. 1 is an overview of an embolic protection filter assembly.

FIG. 1 illustrates an example embolic protection filter assembly 10 that can be manufactured according to at least some of the methods disclosed herein. Assembly 10 includes an elongate shaft or guidewire 12 having an embolic protection filter 14 coupled thereto. Filter 14 includes a filter material 16 coupled to a filter frame 18 (not shown in FIG. 1, best seen in FIG. 3). In general, filter 14 may be adapted to operate between a first generally collapsed configuration and a second generally expanded configuration for collecting debris in a body lumen. Frame 18 may be comprised of a "self-expanding" shape-memory material such as nickel-titanium alloy (to bias filter 14 to be in the second expanded configuration). Additionally, frame 18 may include a radiopaque material or include, for example, a radiopaque wire disposed about a portion thereof. Filter material 16 can be drilled (for example, formed by known laser techniques) or otherwise manufactured to include at least one opening 20. The holes or openings 20 are sized to allow blood flow therethrough but restrict flow of debris or emboli floating in the body lumen or cavity. One or more struts 22 may extend between frame 18 and shaft 12 and be coupled to shaft 12 by a coupling 24. Coupling 24 may be one or more windings of struts 22 about shaft 12 or be a fitting disposed over an end of struts 22 to attach it to shaft 12.

Figure 2:
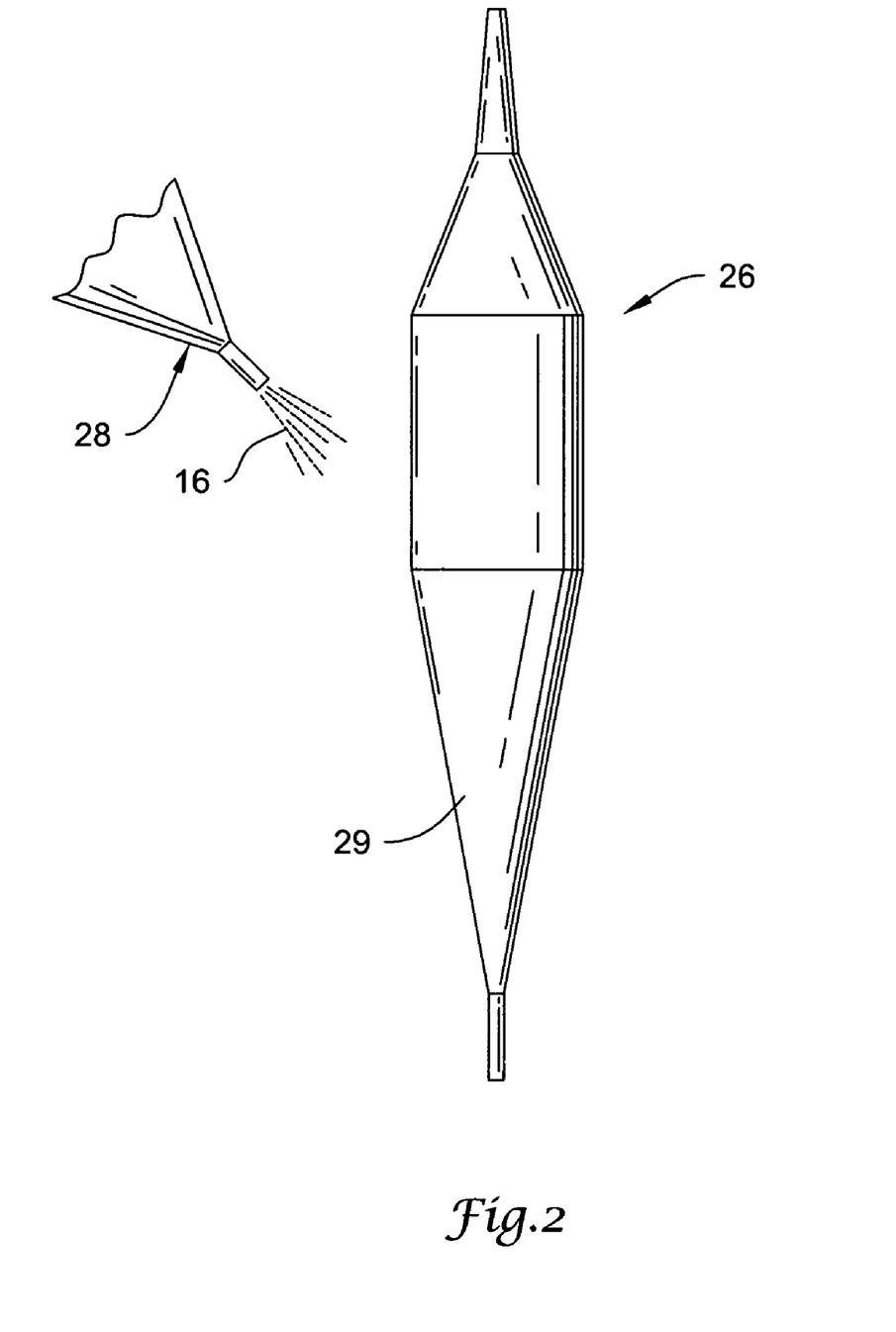
FIG. 2 is a perspective view of a filter material being spray coated onto a forming member or spray mold.

In at least some embodiments, filter 14 may be formed by powder or spray coating filter material 16 onto a forming member or spray mold 26 as shown in FIG. 2. Filter material 16 may be subjected to one or more processing steps in order to facilitate spraying. For example, filter material 16 may be provided in a particulate form or ground to a particulate powder or resin. The resin can be combined with flow modifiers or other suitable additives, extruded, and ground into a powder of the desired particle size. The particulate or powdered filter material 16 can spray coated onto spray mold 26 with known spray coating equipment and techniques. The spray coated spray mold 26, including filter material 16, may be heated (e.g., in an oven) to define filter 14

Alternatively, a solution of filter material 16 may be spray coated onto spray mold 26. According to this embodiment, filter material 16 may comprise a liquid or may comprise a material that is put into solution, for example, by an appropriate solvent. Additionally, filter material 16 as a solution may be combined with appropriate resins or binders and sprayed. Filter material 16 as a solution may be directly sprayed onto spray mold 26 similar to how a powder filter material 16 can be. In at least some embodiments, filter material 16 as a solution may not need any heating to form and/or define filter 14. Instead, filter 14 may be defined when filter material 16 dries and/or any solvent evaporates or is removed.

It can be appreciated that a plurality of spray coatings may be applied to spray mold 26 depending on the desired configuration of filter 14. For example, in some embodiments it may be desirable to manufacture filter 14 by spray coating a single layer or coat of filter material 16 onto spray mold 26. Alternatively, other embodiments include manufacturing filter 14 by powder coating a plurality of layers. According to this later embodiment, subsequent layers may be spray coated onto earlier layers. However, in embodiments where multiple layers are sprayed onto spray mold 26, the individual layers may be comprised of different materials, may be of different thicknesses, may cover different portions of spray mold 26, etc.

The composition of filter material 16 (whether a single or multiple layer configuration is used) may include essentially any appropriate polymer or other suitable materials. Some examples of suitable polymers include polyurethane, polyether-ester (for example a polyether-ester elastomer such as ARNITEL® available from DSM Engineering Plastics), polyester (for example a polyester elastomer such as HYTREL® available from DuPont), or linear low density polyethylene (for example REXELL®), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene, Marlex high-density polyethylene, polyetheretherketone (PEEK), polyimide (PI), and polyetherimide (PEI), a liquid crystal polymer (LCP) alone or blended with other materials, and the like, or mixtures, combinations, or copolymers thereof. Alternatively, filter material 16 may be comprised of SOL-GEL.

In some embodiments, filter material 16 may include or otherwise be doped with a therapeutic coating (not shown but it can be appreciated that the coating may itself be a layer of filter material 16, be disposed onto a layer of filter material 16, be imbedded or doped within filter material 16, or be disposed between layers of filter material 16). Some examples of therapeutic coatings may include may include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, anti-thrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; and cholesterol-lowering agents; vasodilating agents; agents which interfere with endogenous vascoactive mechanisms; anti-sense DNA and RNA; and DNA coding for (and the corresponding proteins) anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, and the family of bone morphogenic proteins ("BMP's") including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, BMP-16, "hedgehog" proteins.

Additionally, in some embodiments, a lubricious (e.g., hydrophylic) or other type of coating may be applied over portions or all of filter material 16 and/or over portions of spray mold 26. Hydrophobic coatings such as fluoropolymers, including polytetrafluroethylene (PTFE), provide a dry lubricity that may, for example, allow filter material 16 to more easily separate from spray mold 26. Suitable lubricious polymers are well known in the art and may include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

Spray mold 26 may be comprised of an appropriate material such as a metal. Alternatively, spray mold 26 may be comprised of a dissolvable material in order to facilitate the removal of filter material 16 from spray mold 26. For example, spray mold 26 may be comprised of water soluble substance (such as sodium chloride or other soluble salts) or polymer such as the poly(ethylene oxide). In at least some embodiments, the dissolvable spray mold 26 may be formed by molding a negative or reverse spray mold from a typical metal spray mold and then using the negative to mold the "sacrificial" spray mold 26. It can be appreciated that a number of different materials and methods of manufacturing can be utilized to form spray mold 26 without departing from the spirit of the invention.

The shape of spray mold 26 may generally include a filter-shaped distal portion 29 where filter material 16 may be sprayed onto in order to form a typically shaped filter 14. However, it can be appreciated that shape of spray mold 26 can be altered in order to manufacture filter 14 having essentially any shape including a typical or unusual shapes. For example, spray mold 26 and/or distal portion 29 may be adapted to be more rounded, cylindrical, elliptical, elongated, or any other desired shape.

In at least some embodiments, spray mold 26 may be pre-sprayed with a priming layer or tie layer of material. The priming or tie layer may provide a number of desirable features. For example, the priming layer may help improve the adhesion of filter material 16 to spray mold 26. Additionally, the priming layer may also help facilitate the removal of filter 14 from spray mold 26.

The one or more layers of filter material 16 may be sprayed onto a portion (e.g., distal portion 29) of spray mold 26 by a spray gun or nozzle 28 connected to typical spray coating equipment (not shown). Spraying may occur directly onto spray mold 26 or onto the priming layer or tie layer as described above. To facilitate the adhesion of filter material 16 to spray mold 26, spray mold 26 may be comprised of metal or another electrically conductive material. According to this embodiment, electrical potential (voltage) may be inherently present within or otherwise applied to spray mold 26. Filter material 16 may also be electrically charged. Then, when filter material 16 leaves the front of spray gun 28, the electrical state of spray mold 26 attracts the charged filter material 16. It can be appreciated that alterations in the amount of voltage, spray time, the distance between spray gun 28 and spray mold 26, and other similar parameters are within the scope of the invention.

In some embodiments, spray mold 26 may be rotated so that spray gun 28 can powder coat all sides of spray mold 26. Because the rotation of spray mold 26 may be controlled by machine that allows for precise coordination of spray mold 26 and spray gun 28, spinning spray mold 26 may permit the technician to precisely control the thickness of filter 14. For example, it may be possible to construct filters 14 that include a filter material 16 that is very thin (e.g., about 0.001 inches or less).

In some embodiments, when an appropriate amount of filter material 16 has been spray coated onto spray mold 26, spray mold 26 may be heated by an oven, heater, or other suitable heating device. Heating spray mold 26 allows filter material 16 to at least partially melt and fuse together as well as remove (e.g., via evaporation) solvents, fillers, additive, or other unwanted materials. The temperature required to fuse the filter material 16 and the amount of time the components are subjected to heating may vary in embodiments where different materials or configurations are utilized. For example, the temperature of the oven may be about 300–500 degrees Fahrenheit or more and the baking time may be about 5 to 20 minutes or more. It can be appreciated, however, that some embodiments of the invention include the use of materials and steps that may not include heating in order to define filter 16. For example, filter material 16 may comprise a solution that sprayed onto spray mold 26 and filter 14 may be defined when filter material 16 dries as described above.

Once fused or otherwise formed or defining filter 14, filter material 16 may be subjected to a number of additional manufacturing steps. For example filter material 16 may be coupled to shaft 12 and/or a filter frame 18. Additionally, filter material 16 may be drilled or otherwise manufactured to have a plurality of holes formed therein. A number of methods and devices may be used to form the holes, for example typical laser drilling devices. In some embodiments, holes may be spaced longitudinally about 50–150 µM (e.g., about 109 µM) and axially about 50–150 µM throughout filter material 16. Additionally, the diameter or size of holes may also be controlled. For example, holes may have diameter in the range of about 50–150 µM (e.g., about 80 µM).

Another appropriate way of forming holes within filter material 16 may include spraying an intermediate substance onto filter material 16. The intermediate substance may comprise a substance, compound, mixture, solvent, acid, base, etc. that is reactive with filter material 16 so that it dissolves filter material 16 at locations where the intermediate substance comes into contact with filter material 16. Alternatively, a second intermediate substance may be sprayed over portions of the first intermediate substance. According to this embodiment, the first intermediate substance is not directly reactive with filter material 16. However, the second intermediate substance is reactive with the first so that the result of the reaction of the first and second intermediate substances is dissolution of filter material 16 at the desired locations, which defines holes in filter material 16.

Figure 3:
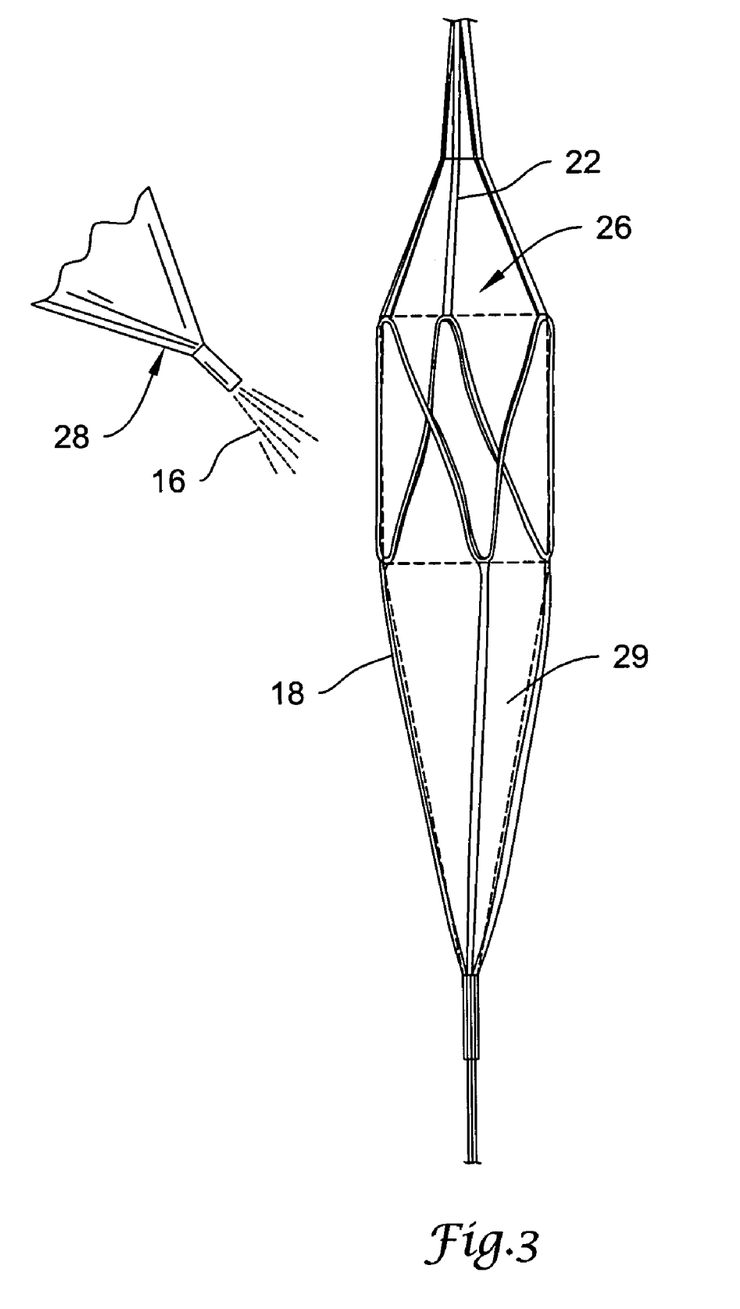
FIG. 3 is a perspective view of a filter material being spray coated onto a spray mold and a filter frame.

In some embodiments, it may be desirable to dispose filter frame 18 over a portion of spray mold 26 and spray filter material 16 over frame 18 (and spray mold 26) as shown in FIG. 3. Frame 18 may be comprised of a metal such as stainless steel, a metal alloy such as nickel-titanium alloy, a polymer, or other suitable materials, combinations of materials, and the like. Frame 18 may be generally configured to provide structural support to filter 14 and may include one or more struts 22 that can be arranged to extend between filter 14 and shaft 12.

Figure 4:
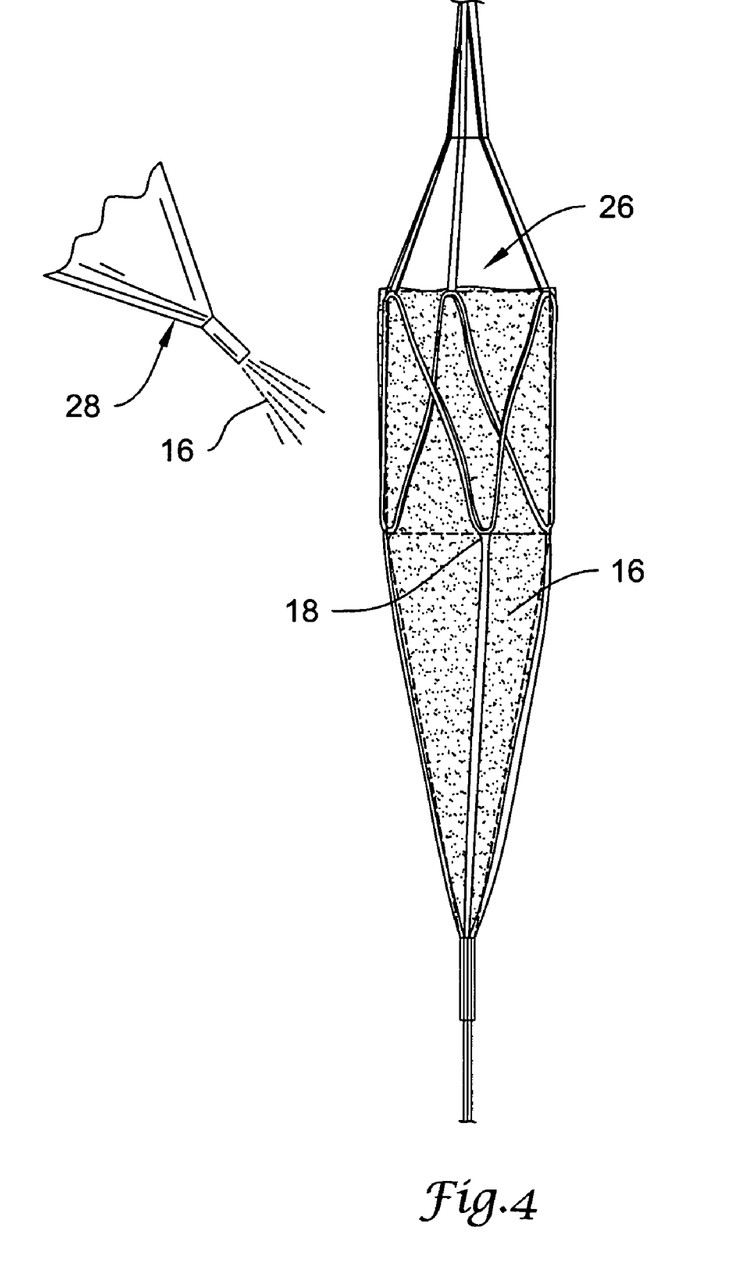
FIG. 4 is a perspective view of a second layer of filter material being sprayed onto a spray mold having a first layer of filter material and a support member.
Figure 5:
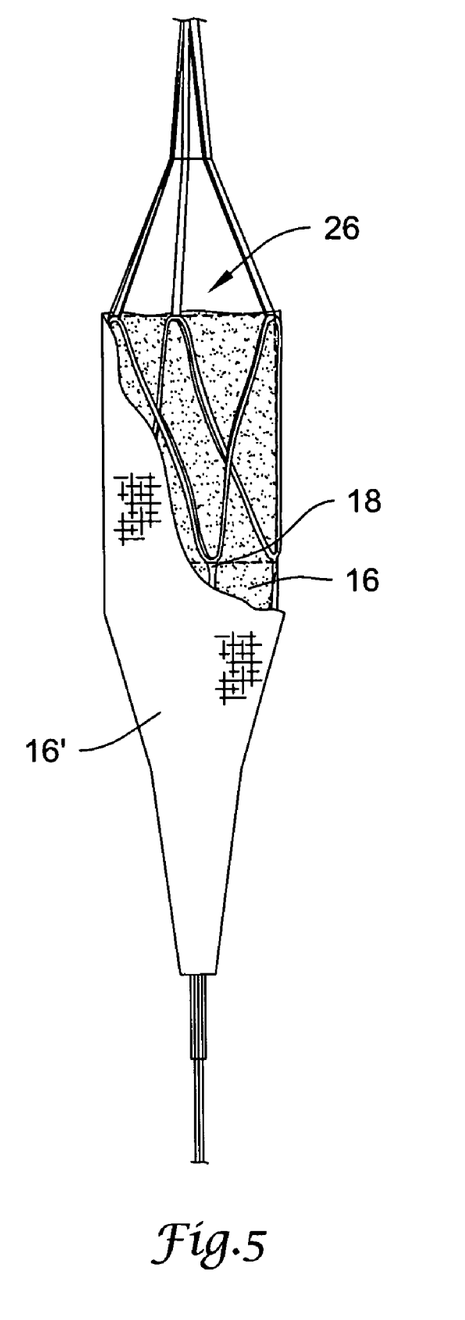
FIG. 5 is a partially cut away perspective view of a first layer of filter material, a support member, a second layer of filter material, and the spray mold.

Filter material 16 may be sprayed directly onto frame 18 or, alternatively, frame 18 can be disposed or "sandwiched" between a first and a second layer of filter material 16 as shown in FIGS. 4 and 5. According to this embodiment, it is possible to couple frame 18 and filter material 16 without increasing the size or thickness of filter 14. For example, the first layer of filter material 16 may be sprayed onto spray mold 26 so that it has a thickness (e.g., about 0.0005 to about 0.001 inches or less) that is only a portion of the thickness of typical filter materials (e.g., about 0.001 to about 0.002 inches) as shown in FIG. 4. Frame 18 may then be disposed over the first layer and then a second layer of filter material (shown cut away in FIG. 5 and indicated by reference number 16') may be spray coated over the first layer and frame 18 as shown in FIG. 5. The thickness of the second layer of filter material 16 may, again, be about one-half the thickness of typical filter materials.

Figure 6:
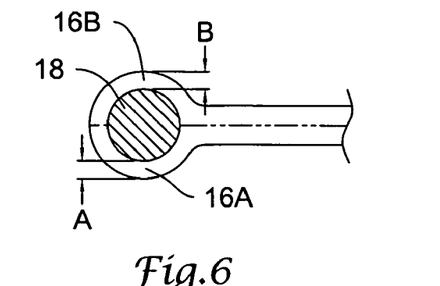
FIG. 6 is a cross-sectional view taken through an example embolic protection filter.

A cross-sectional view of filter 14 that illustrates the frame 18 disposed between layers of filter material 16 is shown in FIG. 6. In this figure, a first layer of filter material 16a is shown having a thickness A. Frame 18 is disposed over first layer 16a. A second layer of filter material 16b having a thickness B is disposed over first layer 16a and frame 18. In some embodiments, thicknesses A and B are about equal and are each about one-half the thickness of a typical filter as described above. Thus, the end result of this strategy is filter material 16 having a thickness that is not increased relative to typical filters. Maintaining or otherwise reducing the size of filter material 16 may be desirable, for example as a part of interventions where dimensions are small or the target site is fragile such as the neural vasculature.

The above strategy for coupling filter material 16 to frame 18 may have several desirable properties in addition to the ability to avoid increasing the size or profile of filter 14. For example, this strategy may allow frame 18 to be coupled to filter material 16 without the need for adhesives. Additionally, this strategy may simplify the manufacturing process and reduce manufacturing time. For example, this embodiment obviates any need to detach the filter material from the spray mold, invert or prolapse the filter material, attach the frame with an adhesive, and then revert the filter material as might be required by other manufacturing methods. It can be appreciated that the present invention includes alterations to the method and assemblies illustrated in FIGS. 4–6. For example, the shape of frame 18 may be altered to that of a filter mesh or other suitable structure. Alternatively, frame 18 may be comprised of, coated with, or attached to a radiopaque material that would allow a clinician to visualize filter 14.

Figure 7:
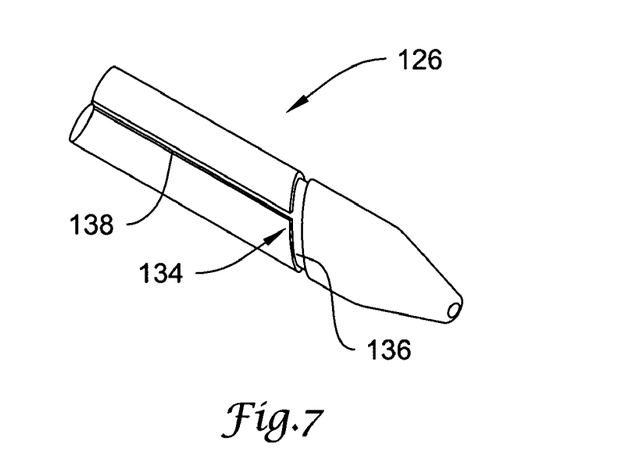
FIG. 7 is a perspective view of another example spray mold for manufacturing an embolic protection filter.
Figure 7A:
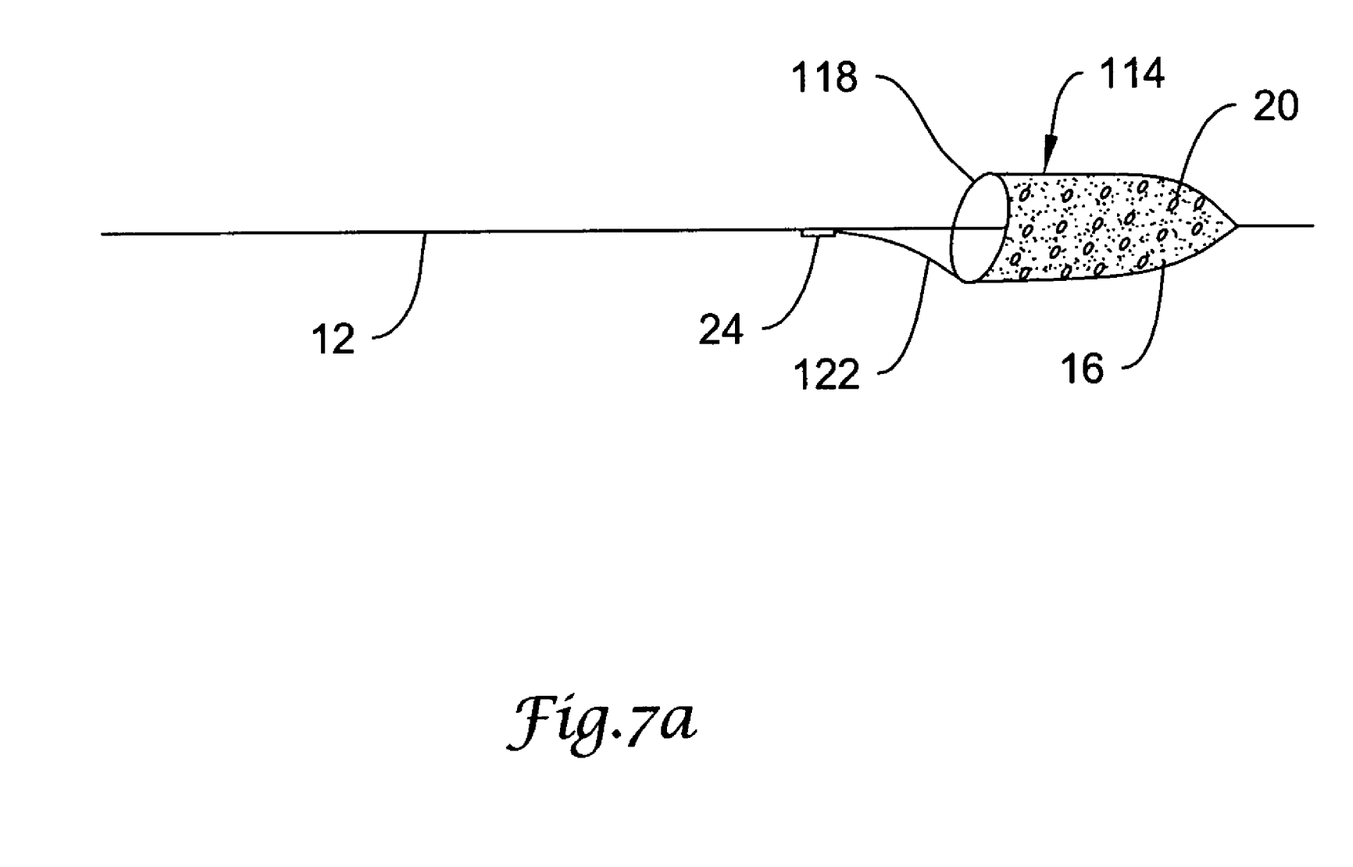
FIG. 7A is an alternative embodiment of a spray molded filter.

FIG. 7 is a perspective view of another example spray mold 126 for manufacturing another example embolic protection filter 114 (illustrated in FIG. 7A). Spray mold 126 is essentially the same in form and function as spray mold 26 except that it includes one or more grooves 134. In at least some embodiments, grooves 134 include a filter mouth defining portion 136 and a strut defining portion 138. According to these embodiments, a shaft or frame (e.g., like frame 18) may be disposed within or adjacent grooves 134 at the above portions 136/138 to define a filter mouth and strut (e.g., strut 22) for filter 114.

In at least some embodiments, spray mold 126 (as well as any spray mold described herein) may be used in conjunction with spinning techniques and/or equipment. For example, spray mold 126 may be configured to spin and/or have filter material 16 spun thereon. The exact arrangement of the shaft or frame and filter material 16 may vary. For example, a first layer of filter material 16 may be spun or otherwise disposed over spray mold 126 (e.g., by spinning about 40 passes or more of filter material 16), the shaft or frame may then be disposed over the filter material 16 and adjacent the grooves 134, and a second layer of filter material 16 may be spun over the first layer and the shaft or frame (again, by spinning about 40 passes or more). In some embodiments, the shaft or frame may be treated with an adhesive or primer to facilitate the joining of the various layers. Moreover, the spray mold 126, filter material 16, and shaft or frame may be heat treated, for example in an oven similar to what is described above. The heat treatment may occur over a range of temperatures (e.g., about 100° C. or greater) and over a range of times (e.g., about 15–30 minutes or longer).

FIG. 7A illustrates an example of a filter 114 that can be manufactured from spray mold 126. Filter 114 is essentially the same in form and function as filter 14, except that it includes a single strut 122 and that frame 118 is generally disposed at the filter mouth. It can be appreciated, however, that alterations to spray mold 126 that include additional grooves 134 for manufacturing a multi-strut filter like filter 14 of FIG. 1 are within the scope of the invention. Moreover, grooves 134 can also be altered so that frame 118 can be disposed over spray mold 126 analogously to how frame 18 is disposed over spray mold 26 in FIG. 3 as described below.

Figure 8:
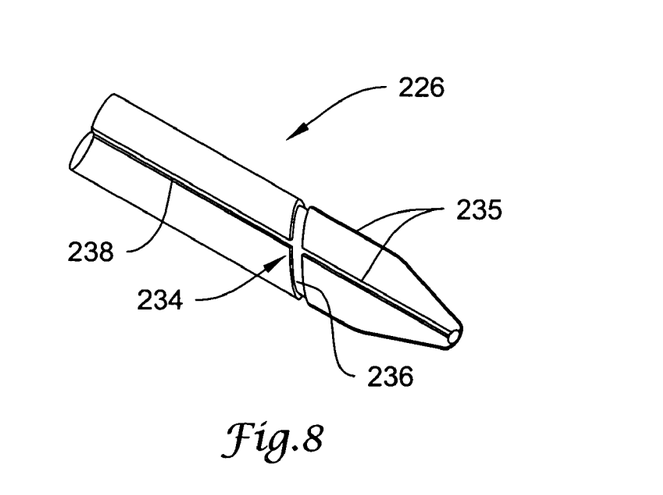
FIG. 8 is a perspective view of another example spray mold for manufacturing an embolic protection filter.

FIG. 8 is a perspective view of another example spray mold 226 that is essentially the same in form and function as spray mold 126, except that grooves 234 have an alternative arrangement. This alternative arrangement results in grooves 234 including a set of longitudinal extensions 235 in addition to filter mouth defining portion 236 and strut defining portion 238. In some embodiments, longitudinal extensions 235 of grooves 234 are adapted and configured for being disposed essentially where frame 18 may be disposed on spray mold 226. This arrangement may allow frame 18 to held in place within longitudinal extensions 235 of grooves 234 if it is desirable to incorporate frame 18 into the construction of filter 14.

Figure 9:
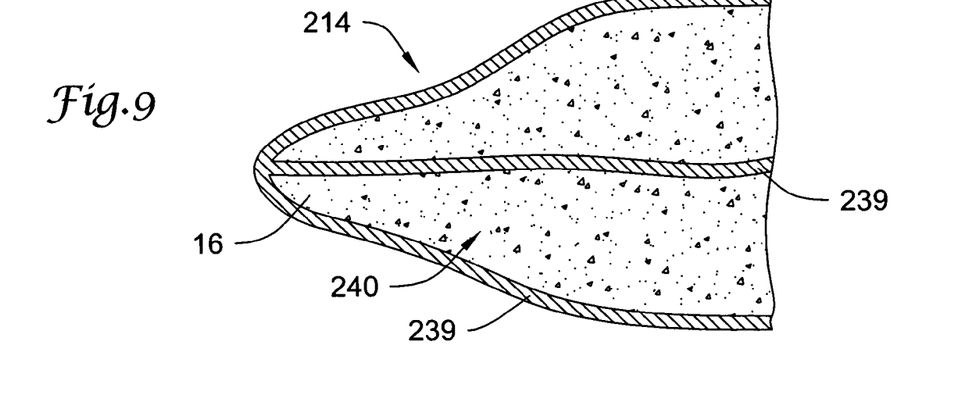
FIG. 9 is a partial cross-sectional view of a portion of example embolic protection filter.

Alternatively, longitudinal extensions 235 of grooves 234 may provide a position for filter material 16 to be thickened so as to provide support or strength. For example, FIG. 9 illustrates another example filter 214 that may be manufactured using spray mold 226. According to this embodiment, filter material 16 may be powder or spray coated (or dip molded) so that longitudinal extensions 235 become filled with filter material 16. Thus, the thickness or amount of filter material 16 disposed on spray mold 226 may be greater adjacent longitudinal extensions 235. These thickened regions of filter 214, which are indicated in FIG. 9 by reference number 239, may be configured to provide the desired amount of structural support (i.e., similar to that of frame 18), for example adjacent the solid, non-drilled portions of filter 214. Moreover, this embodiment allows the reinforcing structure to be comprised of the same material as other parts of the filter material 16, which may simplify the manufacturing process.

Grooves 234 (for example at longitudinal extensions 235) may be oriented inward within spray mold 226 (as shown in FIG. 8) so as to created thickened regions 239 of filter material on the inside surface 240 of filter 214. Alternatively, grooves 234 could be oriented outward or otherwise configured so that thickened regions 239 are disposed on the outside surface of filter 214. In still other embodiments, grooves 234 may be configured so that thickened regions 239 are disposed and extend from both inside surface 240 and the outside surface of filter 214.

FIG. 9 is a partial cross-sectional view of a portion of filter 214 that illustrates thickened regions 239 disposed along an inside surface 240. It should be emphasized that only a portion of filter 214 is illustrated in FIG. 9 and that some of the other structural elements of the embolic protection filter assembly that can be included with the use of filter 214, for example shaft 12, struts such as struts 22/122, coupling 24, etc. have been omitted. Thus, only a portion of inside surface 240 has been drawn in order to illustrate that thickened regions 239 are oriented inward relative to inside surface 240. Additionally, thickened regions 239 are indicated to extend from inner surface 240 by cross-section line hatching, which indicates that the cross-section viewed in FIG. 9 is taken relatively close to an edge or border of filter 214.

Figure 10:
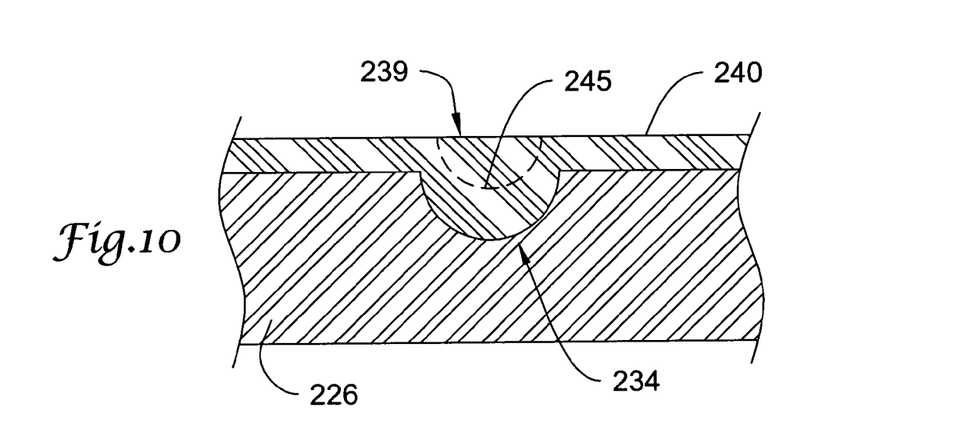
FIG. 10 is a cross-sectional view of a portion of an example embolic protection filter.

In at least some embodiments, the shape of grooves 234 (including longitudinal extensions 235 or other appropriate structures) and/or thickened regions 239 of filter material 240 may vary to include essentially any shape. FIGS. 10–16 illustrate some examples of the various shapes and configurations. For example, FIG. 10 illustrates that grooves 234 may be generally rounded in shape and that thickened regions 239 may also be rounded. In some embodiments, thickened regions 239 can have an increased thickness as shown in FIG. 10, which may be desirable for at least some of the reasons stated above. Alternatively, filter material 240 may be sprayed onto spray mold 226 so that the shape of filter material 240 is similar to groove 234. This variation that may define a shaped region 245 is shown by phantom lines in FIG. 10.

Figure 11:
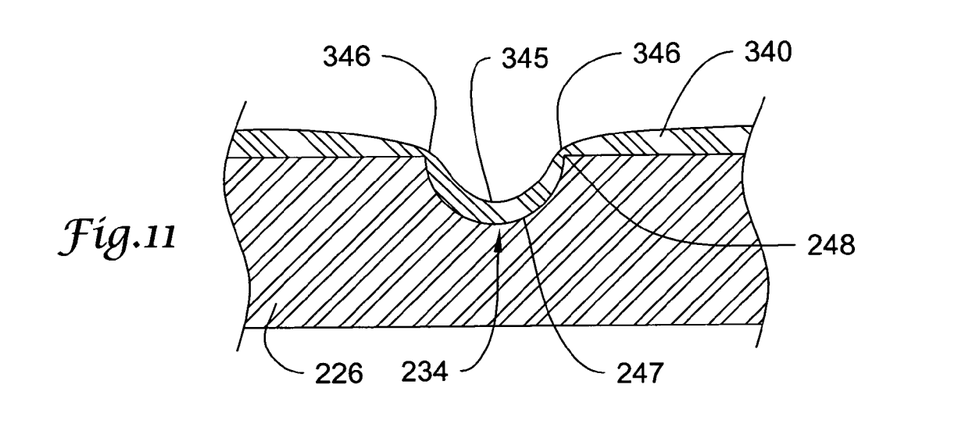
FIG. 11 is an alternative cross-sectional view of a portion of an example embolic protection filter.

Shaped region 245 may also include other features. For example, FIG. 11 illustrates that the shape of groove 234 may allow for one or more thinned spots 346 to be defined adjacent shaped region 345 when spraying filter material 340. Because of the projecting shape of groove 234, its protrusion 247 may be able to catch or hold greater quantities of filter material 340 than its shoulders 248. Additionally, sloping adjacent shoulders 248 may result in some flowing or migrating of filter material 340 from positions adjacent shoulders 248 toward protrusion 247. Thus, spraying filter material 340 onto spray mold 226 may result in thinned spots 346, for example, adjacent shoulders 248.

Thinned spots 346 may be desirable for a number of reasons. For example, thinned spots 346 may help facilitate the folding of filter material 340 and the resultant filter manufactured with filter material 340. This may be because thinned spots 346 have less filter material 340 and, thus, may fold easier. Additionally, because the location of thinned spots 346 can be varied by altering the distribution or position of grooves 234 in spray mold 226, it may be possible for the folding pattern for a filter to be controlled during manufacturing. For example, a manufacturer may be able to create filters with consistent and known folding patterns or characteristics.

Figure 12:
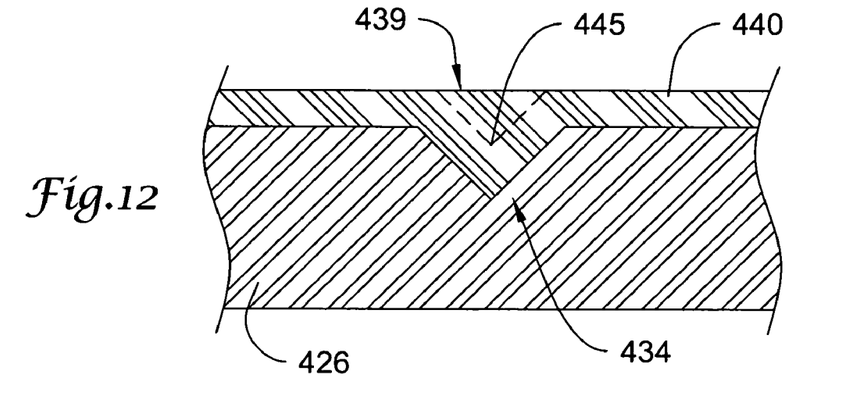
FIG. 12 is an alternative cross-sectional view of a portion of an example embolic protection filter.

FIG. 12 illustrates another example shape variation for filter material 440. According to this embodiment, thickened regions 439 may be generally pointed in shape when spray molded onto mandrel 426 with pointed grooves 434. Similar to what is described above, filter material 440 may be sprayed to define thickened region 439 or to define shaped region 445 as shown in phantom lines.

Figure 13:
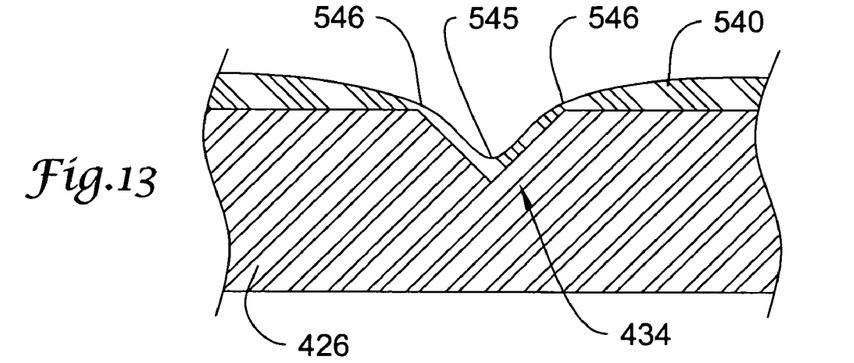
FIG. 13 is an alternative cross-sectional view of a portion of an example embolic protection filter.

FIG. 13, much like in FIG. 11 above, illustrates that at least some embodiments may result in thinned spots 546 being defined in filter material 540. Thinned spots 546 adjacent shaped region 545 may result from the shape of groove 434 and may have desirable characteristics including those listed above.

Figure 14:
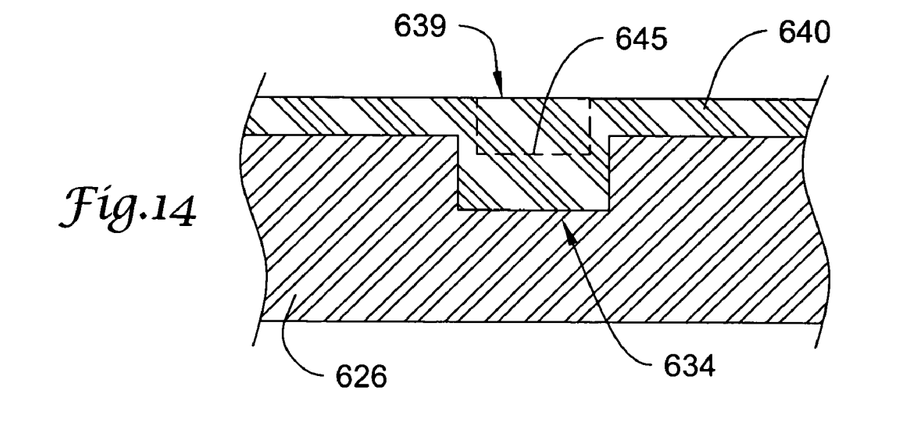
FIG. 14 is an alternative cross-sectional view of a portion of an example embolic protection filter.
Figure 15:
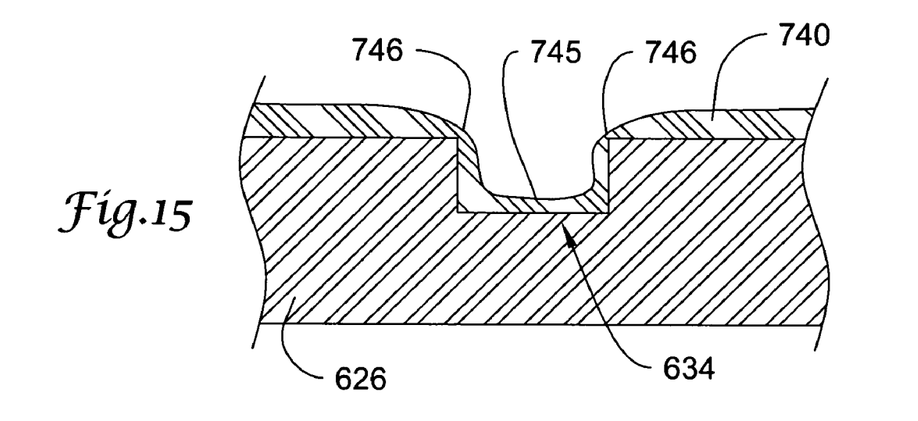
FIG. 15 is an alternative cross-sectional view of a portion of an example embolic protection filter.

FIG. 14 illustrates another example shape variation for filter material 640. According to this embodiment, thickened regions 639 may be generally squared in shape when spray molded onto spray mold 626 with squared grooves 634. Similar to what is described above, filter material 640 may be sprayed to define thickened region 639 or to define shaped region 645 as shown in phantom lines. Additionally, FIG. 15, much like in FIGS. 11 and 13 above, illustrates that at least some embodiments may result in thinned spots 746 being defined in filter material 740. Thinned spots 746 adjacent shaped region 745 may result from the shape of groove 634 and may have desirable characteristics including those listed above.

Figure 16:
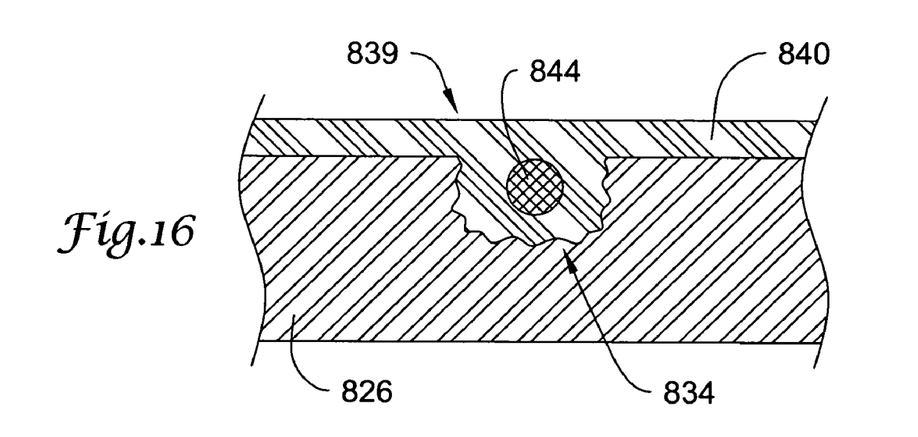
FIG. 16 is an alternative cross-sectional view of a portion of an example embolic protection filter.

FIG. 16 illustrates another example shape variation where thickened regions 839 of filter material 840 may an irregular shape when filter material 840 is sprayed onto spray mold 826 having irregularly shaped grooves 834. FIG. 16 also illustrates that thickened regions 839 may also include a support or imaging structure 844 disposed therein. For example, structure 844 may comprise a radiopaque wire or material similar to those described above. Alternatively, structure 844 may comprise an alternative polymer or frame similar to frame 18. Structure 844 may be incorporated into thickened region 839 by spray coating a layer of filter material 840 onto grooves 834, disposing structure 844 adjacent grooves 834 (and the layer of filter material 840), and then spraying additional layer(s) of filter material 840 over structure 844.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of manufacturing an embolic protection filter assembly, comprising the steps of:
   providing a forming member;
   providing a filter material;
   providing a filter frame;
   disposing the filter frame over at least a portion of the forming member; and
   spray coating the filter material onto at least a portion of the forming member to define a filter.

2. The method of claim 1, further comprising the step of heating the filter material.

3. The method of claim 1, further comprising the step of forming a plurality of holes in the filter.

4. The method of claim 3, wherein the step of forming a plurality of holes in the filter includes laser drilling.

5. The method of claim 3, wherein the step of forming a plurality of holes in the filter includes spraying a first intermediate substance onto the filter and then spraying a second intermediate substance onto the first intermediate substance that reacts with the first intermediate substance and the filter, thereby dissolving the filter at locations where the first intermediate substance, second intermediate substance, and filter have reacted.

6. The method of claim 1, wherein the filter has a thickness and wherein the step of spray coating the filter material onto at least a portion of the forming member includes spray coating a first quantity of filter material onto the forming member that has a thickness that is about one half the thickness of the filter.

7. The method of claim 6, wherein the filter frame is disposed over the first quantity of filter material.

8. The method of claim 7, further comprising the step of spray coating a second quantity of filter material over the filter frame, wherein the second quantity of filter material has a thickness that is about one half the thickness of the filter.

9. The method of claim 1, further comprising the step of dissolving the forming member.

10. A method of manufacturing an embolic protection filter assembly, comprising the steps of:
    providing a forming member;
    providing a filter material; and
    spray coating the filter material onto at least a portion of the forming member to define a filter;
    wherein the forming member has one or more grooves and wherein the step of spray coating the filter material onto the forming member includes increasing the thickness of the filter adjacent the grooves.

11. The method of claim 10, wherein the grooves are squared in shape.

12. The method of claim 10, wherein the grooves are pointed in shape.

13. The method of claim 10, wherein the grooves have an irregular shape.

14. A method of manufacturing an embolic protection filter, comprising the steps of:
providing an electrically conductive forming member having a filter forming region; and
spraying an electrically charged filter material onto the filter forming region to define a filter
wherein the forming member includes one or more grooves.

15. The method of claim 14, further comprising the step of heating the filter material adjacent the filter forming region so that the filter material melds together to define a filter.

16. The method of claim 14, wherein the step of spraying an electrically charged filter material includes spraying filter material into the grooves.

17. The method of claim 14, further comprising the step of dissolving the forming member.

18. A method of manufacturing an embolic protection filter, comprising the steps of:
providing an electrically conductive forming member having a filter forming region;
spraying an electrically charged filter material onto the filter forming region to define a filter; and
disposing a filter frame over the forming member.

19. A method of manufacturing an embolic protection filter, comprising the steps of:
providing a forming member including one or more grooves, the grooves including a projection and a shoulder region;
spray coating a filter material onto the forming member adjacent the grooves to define a filter; and
thinning a portion of the filter material adjacent the shoulder region of the grooves.

20. The method of claim 19, wherein the step of spray coating a filter material onto the forming member includes spray coating a powdered filter material.

21. The method of claim 19, wherein the step of spray coating a filter material onto the forming member includes spray coating a solution of filter material.

* * * * *